United States Patent [19]

Waldmeier et al.

[11] 4,284,638
[45] Aug. 18, 1981

[54] PHARMACEUTICAL COMPOSITIONS WITH CENTRAL DEPRESSANT AND ANTIPSYCHOTIC ACTIVITY, WHICH CONTAIN AS ACTIVE INGREDIENTS, A BUTYROPHENONE DERIVATIVE WHICH IS BASICALLY SUBSTITUTED IN THE 4-POSITION AND A C-(2-BENZOFURANYL)-PIPERIDINE OR C-(2-BENZOFURANYL)-TETRAHYDROPYRIDINE

[75] Inventors: Peter Waldmeier, Reinach; Aleksandra Delini-Stula, Basel, both of Switzerland

[73] Assignee: Ciba-Geigy Corporation, Ardsley, N.Y.

[21] Appl. No.: 93,970

[22] Filed: Nov. 14, 1979

[30] Foreign Application Priority Data

Nov. 21, 1978 [CH] Switzerland .................. 11918/18

[51] Int. Cl.³ .................................. A61K 31/445
[52] U.S. Cl. ............................ 424/267; 424/263; 546/196; 546/217; 546/269
[58] Field of Search ............... 424/267, 263; 546/196, 546/199, 217, 225, 269

[56] References Cited

U.S. PATENT DOCUMENTS

| 3,097,209 | 7/1963 | Janssen | 546/225 |
| 3,161,645 | 12/1964 | Janssen | 546/199 |
| 3,438,991 | 4/1969 | Janssen | 546/217 |
| 3,518,276 | 6/1970 | Janssen | 546/217 |
| 4,210,655 | 7/1980 | Schenker et al. | 546/296 |

FOREIGN PATENT DOCUMENTS 2408476 9/1974 Fed. Rep. of Germany .......... 546/269
1,465,581 2/1977 United Kingdom .................. 546/196

OTHER PUBLICATIONS

C. J. Carter and C. J. Pycock, in (Proceedings Mar., 1977) "British Journal of Pharmacology", vol. 60, pp. 267 P-268 P, (1977).
G. Stille, "Schweizerische Medizinische Wochenschrift", vol. 99, pp. 1645-1654 and 1690-1693, (1969).
Chemical Abstracts, Index Guide, (1977), p. 485 G and p. 825 G.
Waldmeier et al., European J. of Pharmacology, vol. 55, (1979), pp. 363-373.

Primary Examiner—Robert T. Bond
Attorney, Agent, or Firm—Prabodh I. Almaula

[57] ABSTRACT

The invention relates to pharmaceutical compositions which contain, as active ingredients, a butyrophenone derivative I which is basically substituted in the 4-position and has central depressant and antipsychotic activity, or a pharmaceutically acceptable acid addition salt thereof, and an unsubstituted or substituted C-(2-benzofuranyl)-piperidine or C-(2-benzofuranyl)-tetrahydropyridine of the general formula II

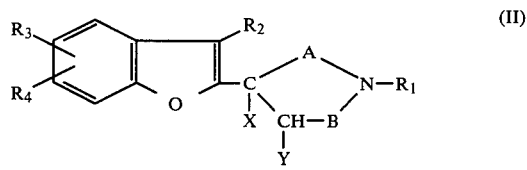

wherein $R_1$ is hydrogen, an alkyl group containing at most 4 carbon atoms, the allyl, 3-oxobutyl, 3-hydroxybutyl, 2-propynyl or cyclopropylmethyl group, $R_2$ is hydrogen or a methyl group, $R_3$ is hydrogen, halogen having an atomic number up to 35, a lower alkyl or alkoxy group, the trifluoromethyl group or a cycloalkyl group containing 5 to 8 carbon atoms, $R_4$ is hydrogen, a lower alkyl group or halogen having an atomic number up to 35, or $R_3$ and $R_4$ together are a 1,3-butadienylene radical in the 4,5-position, corresponding to a fused benzene ring, or a trimethylene radical in the 5,6-position, A is the ethylene group and B is the methylene group, or A is the methylene group and B is the ethylene group, and each of X and Y is hydrogen or together are an additional bond, or a pharmaceutically acceptable acid addition salt thereof.

10 Claims, No Drawings

PHARMACEUTICAL COMPOSITIONS WITH CENTRAL DEPRESSANT AND ANTIPSYCHOTIC ACTIVITY, WHICH CONTAINS AS ACTIVE INGREDIENTS A BUTYPROPHENONE DERIVATIVE WHICH IS BASICALLY SUBSTITUTED IN THE 4-POSITION AND A C-(2-BENZOFURANYL)-PIPERIDINE OR C-(2-BENZOFURANYL)-TETRAHYDRO-PYRIDINE

The present invention relates to novel pharmaceutical compositions containing, as active ingredients, a basically substituted butyrophenone having a central depressant and antipsychotic activity and a C-(2-benzofuranyl)-piperidine or C-(2-benzofuranyl)-tetrahydropyridine which is unsubstituted or substituted in specific manner, or pharmaceutically acceptable acid addition salts of these bases.

In the main it is possible to treat the same pathological conditions with the novel pharmaceutical compositions as with the known basically substituted butyrophenones alone, but the dosage of these active ingredients can be reduced.

It is known that basically substituted butyrophenones, especially substituted p-fluoro-4-piperidinobutyrophenones, such as 4-[4-(p-chlorophenyl)-4-hydroxy-piperidino]-p-fluorobutyrophenone (haloperidol), p-fluoro-4-[4-hydroxy-4-(m-trifluoromethylphenyl)-piperidino]-butyrophenone (trifluoperidol), and p-fluoro-4-[4-(2-oxo-2,3-dihydro-1H-benzimidazol-1-yl)-piperidino]-butyrophenone (benperidol), possess very strong central depressant and antipsychotic activity, and are widely used in psychiatry e.g. for the treatment of psychomotoric states of agitation, e.g. in cerebral arteriosclerosis and senile dementia, in schizophrenia, manic psychoses and paranoid hallucinatory syndromes.

It is further known e.g. from German Offenlegungsschrift No. 2,408,476 and British patent specification No. 1,465,581 that C-(2-benzofuranyl)-piperidines and -tetrahydropyridines which can be substituted in the 1-position and/or in the aromatic ring in specific manner, inhibit the uptake of serotonin in the midbrain synaptosomes in rats and other species of test animals when administered orally or subcutaneously, and likewise selectively inhibit in rats the A-form of monoamine oxidase and the uptake of noradrenalin in the heart in the same mode of administration. The above mentioned C-(2-benzofuranyl)-piperidines and -tetrahydropyridines furthermore antagonise the action of tetrabenazine in rats when administered intraperitoneally and thus possess an activity spectrum which suggests their utility as antidepressants.

Surprisingly, it has now been found that the central depressant and antipsychotic activity characteristic of the butyrophenone derivatives, such as the cataleptic activity and—especially pronounced—the antagonism of the stereotyped behaviour of rats induced by the administration of apomorphine, is potentiated by optionally substituted C-(2-benzofuranyl)-piperidines which do not exhibit corresponding activity when administered by themselves in any dose. For example, the administration of 0.3 mg/kg p.o. of haloperidol together with 10.0 mg/kg p.o. of 4-(5,6-dimethyl-2-benzofuranyl)-piperidine hydrochloride (DMBP hydrochloride) to rats effects a cataleptic action which commences somewhat more rapidly and wears off earlier, but which on the whole is of about the same strength as that produced by 0.5 mg/kg p.o. of haloperidol alone. The stereotyped behaviour induced in rats by apomorphine was antagonised to a lesser degree by 0.3 mg/kg p.o. of haloperidol alone, and more strongly by 0.45 mg/kg p.o. of haloperidol alone, than by 0.06 mg/kg p.o. of haloperidol after premedication with 10.0 mg/kg p.o. of DMBP hydrochloride. Hence the potentiation of haloperidol is observed in this test in about a six-fold reduction of the effective dose, whereas the potentiation of haloperidol in the catalepsy test is less pronounced and corresponds merely to about a 1.7-fold reduction of the effective dose.

DMBP hydrochloride also potentiates the increase in the concentration of homovanillinic acid (HVA) in the striatum which is induced by different doses of haloperidol and which can be considered as an index of the degree of activation of dopaminergic neutrons. Thus in rats, which were treated in this test with the completely ineffective dose of 10 mg/kg per os of DMBP hydrochloride, 0.03 mg/kg p.o. of haloperidol effects the same increase in the concentration of HVA determined 2 hours later, after the animals had been sacrificed, as the administration of 0.1 mg/kg of haloperidol to rats which had not received premedication; and 0.1 mg/kg p.o. administered to rats which had received premedication effects approximately the same increase as 0.3 mg/kg p.o. of haloperidol administered to rats which had not received premedication, corresponding to a reduction of the equivalent doses of haloperidol to about one third by means of premedication with DMBP hydrochloride. While maintaining an unchanged dose of 0.1 mg/kg p.o. of haloperidol, different doses of DMBP hydrochloride administered 30 minutes previously effect the increases, reported in Table 1, in the concentration of HVA and 3,4-dihydroxyphenylacetic acid (DOPAC) in the striatum of rats sacrificed 2 hours after the administration of haloperidol (n=4–5 per dose).

TABLE 1

| Test type | H mg/kg p.o. | D mg/kg p.o. | HVA ng/g | % of con | DOPAC ng/g | % of con |
|---|---|---|---|---|---|---|
| con | — | — | 332 ± 19 | 100 | 1155 ± 47 | 100 |
| H | 0.1 | — | 462 ± 38 | 139 | 1481 ± 64 | 128 |
| D | — | 1 | 309 ± 15 | 93 | 1006 ± 39 | 87 |
| H + D | 0.1 + | 1 | 834 + 84 | 251 | 2108 ± 92 | 183 |
| D | — | 3 | 344 ± 12 | 104 | 994 ± 72 | 86 |
| H + D | 0.1 + | 3 | 1202 ± 117 | 362 | 2495 ± 159 | 216 |
| D | — | 10 | 318 ± 19 | 96 | 974 ± 56 | 84 |
| H + D | 0.1 + | 10 | 1198 ± 82 | 361 | 2697 ± 193 | 234 | con = untreated controls,
H = haloperidol,
D = DMBP hydrochloride

By means of assays with $H^3$-marked haloperidol it was further possible to determine that DMBP exerts no influence on the metabolism of haloperidol in the striatum and that the cause of the potentiation therefore probably does not reside in the influence on concentration and degradation of haloperidol by DMBP.

On the basis of these experimental findings it may be assumed that the clinical doses of haloperidol and similar neuroleptics can be reduced while the antipsychotic activity remains constant or is even intensified, and, consequently, the side-effects are diminished.

Accordingly, the present invention provides pharmaceutical compositions which contain, as active ingredients, a butyrophenone derivative I which is basically substituted in the 4-position and has central depressant and antipsychotic activity, or a pharmaceutically acceptable acid addition salt thereof, and an unsubstituted or substituted C-(2-benzofuranyl)-piperidine or C-(2-benzofuranyl)-tetrahydropyridine of the general formula II

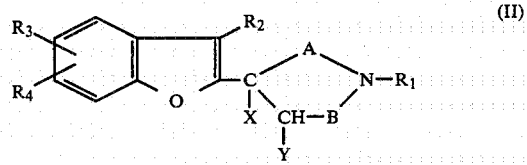

wherein $R_1$ is hydrogen, an alkyl group containing at most 4 carbon atoms, the allyl, 3-oxobutyl, 3-hydroxybutyl, 2-propynyl or cyclopropylmethyl group, $R_2$ is hydrogen or a methyl group, $R_3$ is hydrogen, halogen having an atomic number up to 35, a lower alkyl or alkoxy group, the trifluoromethyl group or a cycloalkyl group containing 5 to 8 carbon atoms, $R_4$ is hydrogen, a lower alkyl group of halogen having an atomic number up to 35, or $R_3$ and $R_4$ together are a 1,3-butadienylene radical in the 4,5-position, corresponding to a fused benzene ring, or a trimethylene radical in the 5,6-position, A is the ethylene group and B is the methylene group, or A is the methylene group and B is the ethylene group, and each of X and Y is hydrogen or together are an additional bond, or a pharmaceutically acceptable acid addition salt thereof.

Suitable compounds of the formula II are in particular those in which $R_1$ is hydrogen, an alkyl radical containing at most 4 carbon atoms, a 2-propynyl or cyclopropylmethyl radical, $R_2$ is hydrogen, $R_3$ is hydrogen, halogen having an atomic number up to 35, a methyl, methoxy or cyclohexyl group, preferably in the 5-position, $R_4$ is hydrogen, a methyl group, chlorine or bromine, A is an ethylene group and B is a methylene group, and X and Y together are an additional bond or preferably each of X and Y is a hydrogen atom. Especially suitable are those compounds of the formula II and of the type singled out for special mention above in which the activity of the inhibition of serotonin uptake in comparison to the other forms of activity is particularly evident. For example, suitable compounds of the general formula II are 4-(6-chloro-2-benzofuranyl)-piperidine and, in particular, 4-(5,6-dimethyl-2-benzofuranyl)-piperidine, and the pharmaceutically acceptable acid addition salts thereof.

The butyrophenone derivatives which are basically substituted in the 4-position are in particular those of the general formula

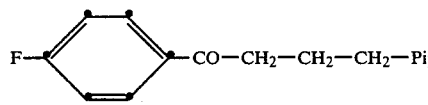

in which Pip is a 4,4-disubstituted or 4-substituted piperidino radical, especially a 4-hydroxy-4-arylpiperidino radical, most preferably a piperidino radical which is substituted in the 4-position by hydroxy and halophenyl, trifluoromethylphenyl or lower alkylphenyl, such as the 4-hydroxy-4-(p-chlorophenyl)-piperidino, 4-hydroxy-4-[m-(trifluoromethyl)-phenyl]-piperidino or 4-hydroxy-4-(p-tolyl)-piperidino radical, the 4-carbamoyl-4-piperidinopiperidino radical or 4-(2-oxo-2,3-dihydro-1H-benzimidazol-1-yl)-piperidino radical.

In the pharmaceutical compositions of the invention the ratio of the butyrophenone derivative I with central depressant and antipsychotic activity to the compound of the general formula II and/or of pharmaceutically acceptable acid addition salts of these active ingredients can vary within wide limits. In general it is between 1:2 and 1:100, preferably between 1:4 and 1:50, and for both the above mentioned active ingredients, in particular between 1:10 and 1:50.

The absolute dosage of both types of active ingredient in the compositions of the invention likewise varies greatly and depends especially on the relative potency of the active ingredients employed, chiefly on that of the butyrophenone derivatives. Dosage units or suitable amounts of formulations not in dosage unit form, e.g. 1 ml of drops or 5 ml of syrup, for administration to warm-blooded animals having an average body weight of about 70 kg, contain e.g. from 0.25 to 2.5 mg of haloperidol or an effective, usually higher, amount of another butyrophenone derivative I with central depressant and/or antipsychotic activity, or of a pharmaceutically acceptable acid addition salt thereof, and 5 to 50 mg, preferably 10 to 25 mg, of a compound of the general formula II or of a pharmaceutically acceptable acid addition salt thereof. Thus pharmaceutical compositions of the invention contain e.g. 0.25 to 2.5 mg, preferably 0.5 to 1 mg, of haloperidol together with 5 to 50 mg, preferably 10 to 25 mg, of 4-(5,6-dimethyl-2-benzofuranyl)-piperidine, if desired in the form of pharmaceutically acceptable acid addition salts. Preferably the compositions of the invention contain the active ingredients together with conventional carriers and/or adjuncts.

In general, one to two dosage units, or corresponding amounts of formulations not in dosage unit form, containing the pharmaceutical compositions of the invention are administered twice or preferably three times daily, so that daily doses correspond preferably to two to six times the above specified single doses. Suitable maintenance doses, however, are also doses which are substantially reduced compared with those specified above.

The present invention is also concerned with the above use of the pharmaceutical compositions for the treatment of the pathological conditions specified herein. The invention also relates to the separate, simultaneous or staggered administration of one or more butyrophenone derivatives I and of one or more compounds of the general formula II, or of pharmaceutically acceptable acid addition salts of these active ingredients, in suitable medicinal formulations, especially in the form of dosage units, in amounts which correspond to the doses contained in the above mentioned combination preparations, for the treatment of the pathological conditions specified above.

The pharmaceutical compositions of the invention are conventional formulations for enteral administration, e.g. tablets, sugar-coated tablets, capsules, suppositories, drops or syrups, or for parenteral administration, especially aqueous injection solutions for intramuscular, intravenous or subcutaneous administration. Solid dosage unit formulations can contain substantially homogeneous mixtures of the active ingredients, or e.g. contain one active ingredient in the core and the other in the coating or in an "inlay" which is compressed into the core, whereby it is also possible to control the release of the active ingredients in a manner known per se by e.g. providing the core or inlay, which preferably contains the much lower dose of butyrophenone derivative I, with a stomach-resistant coating.

The pharmaceutical compositions of this invention are prepared in a manner known per se, for example by conventional mixing, granulating, sugar-coating, solution and lyophilising methods. Thus tablets and sugar-coated tablet cores for oral administration can be obtained by combining the active ingredients with solid carriers, optionally granulating the mixture thereby obtained, and processing the mixture or granules, if desired or necessary after the addition of suitable adjuncts, to tablets or sugar-coated tablet cores.

Examples of suitable carriers are: sugar, e.g. lactose, saccharose, mannitol or sorbitol, conventional cellulose preparations, calcium phosphates, e.g. tricalcium phosphate or calcium hydrogen phosphate, binders, such as starch pastes, for example maize, corn, rice or potato starch paste, gelatin, tragacanth, methyl cellulose, hydroxypropylmethylcellulose, sodium carboxymethylcellulose and/or polyvinylpyrrolidone, also carboxymethyl starch, crosslinked polyvinylpyrrolidone, agar, alginic acid or an alginate, such as sodium alginate, and/or, if desired, disintegrators, such as the above starches. Adjuncts are chiefly glidants and lubricants, for example silicic acid, talc, stearic acid or salts thereof, such as magnesium stearate or calcium stearate, and/or polyethylene glycol. Sugar-coated tablet cores are provided with suitable coatings that can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. By incorporating one or more active components into a suitable carrier which effects a slow release of the active ingredient or ingredients, it is possible to prolong the action of one or more ingredients which in themselves have an action of short duration. Dyes or pigments can be added to the tablets or sugar-coated tablet cores, for example to identify or indicate different combinations of doses of the active ingredients. If desired, it is also possible to provide already obtained tablets with stomach-resistant coatings in order to produce shellac-coated tablets.

Further pharmaceutical compositions for oral administration are dry-filled capsules, and also soft sealed capsules made from gelatin and a plasticizer, such as glycerin or sorbitol. The dry-filled capsules can contain the active ingredient in the form of granules, for example in admixture with fillers such as corn starch, binders and/or lubricants, such as talc or magnesium stearate, and optionally stabilisers. In soft capsules, the active ingredients are preferably dissolved or suspended in suitable liquids, for example in fatty oils, paraffin oil or liquid polyethylene glycols, to which stabilisers, e.g. lecithins, can also be added.

The concentration of active ingredients in liquids for oral administration which are not in dosage unit form, such as syrups and elixirs, is so chosen that a single dose can be readily measured, e.g. as contents of a 5 ml measuring spoon or also as a multiple of this volume. Suitable syrups are e.g. solutions of water-soluble, or suspensions of water-insoluble but absorbable, acid addition salts in aqueous solutions of sugar and/or alkane polyols, such as cane sugar or sorbitol or glycerol, flavourings and aromatic substances as well as optionally preservatives and stabilisers. Elixirs are aqueous-alcoholic solutions of the active ingredients of the invention or of pharmaceutically acceptable salts thereof, which can likewise contain the above additives for syrups. Further suitable formulations for oral administration are drop solutions which usually have a higher alcohol content and at the same time a higher concentration of active ingredients, so that a single dose can be measured e.g. as 10 to 50 drops.

Suitable pharmaceutical compositions for rectal administration are for example suppositories, which consist of a combination of the active components with a suppository base. Examples of suitable suppository bases are natural or synthetic triglycerides, paraffin hydrocarbons, polyethylene glycols or higher alcohols. Gelatin rectal capsules, which consist of a combination of the active components with a base material, can also be employed. Suitable base materials are for example liquid triglycerides, polyethylene glycols or paraffin hydrocarbons.

Ampoule solutions for parenteral, especially intramuscular or intravenous and also subcutaneous, administration contain the active ingredients of the invention in a total concentration of e.g. 0.275 to 5.25% in the form of an aqueous dispersion prepared with the aid of conventional solubilisers and/or emulsifiers and optionally of stabilisers, or preferably in the form of an aqueous solution of pharmaceutically acceptable water-soluble acid addition salts.

The following Examples will serve to illustrate the preparation of two typical formulations, but in no way constitute the sole embodiments thereof.

EXAMPLE 1

Tablets containing 0.025 g of 4(5,6-dimethyl-2-benzofuranyl)-piperidine hydrochloride and 0.001 g of 4-[4-(p-chlorophenyl)-4-hydroxypiperidino]-p-fluorobutyrophenone can be prepared e.g. as follows:

| Composition (for 1000 tablets) | |
| --- | --- |
| 4-(5,6-dimethyl-2-benzofuranyl)-piperidine hydrochloride | 25 g |
| 4-[4-(p-chlorophenyl)-4-hydroxy-piperidino]-p-fluorobutyrophenone | 1 g |
| lactose | 50 g |
| wheat starch | 90 g |
| colloidal silicic acid | 20 g |
| magnesium stearate | 4 g |
| talc | 10 g |
| water | q.s. |

The active ingredients are mixed with a portion of the wheat starch, with the lactose and the colloidal silicic acid and the mixture is passed through a sieve. A further portion of the wheat starch is pasted on a water bath with 5 times the amount of water and the above mixture is kneaded with the resultant paste until a slightly plastic mass is obtained. This mass is forced through a sieve, dried, and the dry granules are passed through a sieve. The remainder of the wheat starch, the talc and the magnesium stearate are then admixed and the resultant mixture is pressed into tablets of 0.2 g.

EXAMPLE 2

Sugar-coated tablets containing 0.025 g of 4-(5,6-dimethyl-2-benzofuranyl)piperidine hydrochloride and 0.001 g of 4-[4-(p-chlorophenyl)-4-hydroxy-piperidino]-p-fluorobutyrophenone can be prepared e.g. as follows:

1000 g of the tablets obtained e.g. by the procedure described in Example 1 are sugar-coated in conventional manner in two steps with a sugar-containing syrup. As such there is used in the first step a syrup consisting of one part of sugar and two parts of water with the addition of talc (18%), polyvinyl pyrrolidone (1.5%) and polyethylene glycol 6000 (1%), and in the second step, a pure sugar syrup.

What is claimed is:

1. A pharmaceutical composition with central depressant and antipsychotic activity which contains, as first active ingredient, a butyrophenone derivative of the formula I

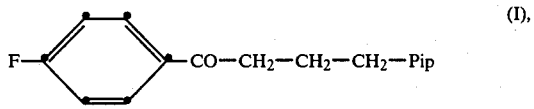

in which Pip is a piperidino radical which is substituted in the 4-position by hydroxyl and a radical selected from halophenyl, trifluoromethylphenyl and lower alkylphenyl, or a pharmaceutically acceptable acid addition salt thereof, and as second active ingredient, an unsubstituted or substituted C-(2-benzofuranyl)-piperidine or C-(2-benzofuranyl)-tetrahydropyridine of the formula II

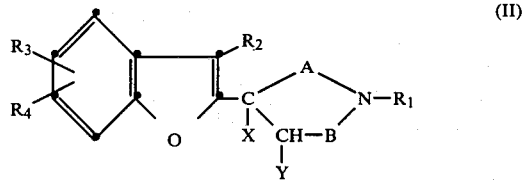

wherein $R_1$ is hydrogen, an alkyl group containing at most 4 carbon atoms, the allyl, 3-oxobutyl, 3-hydroxybutyl, 2-propynyl or cyclopropylmethyl group, $R_2$ is hydrogen or a methyl group, $R_3$ is hydrogen, halogen having an atomic number up to 35, a lower alkyl or alkoxy group, the trifluoromethyl group or a cycloalkyl group containing 5 to 8 carbon atoms, $R_4$ is hydrogen, a lower alkyl group or halogen having an atomic number up to 35, or $R_3$ and $R_4$ together are a 1,3-butadienylene radical in the 4,5-position, corresponding to a fused benzene ring, or a trimethylene radical in the 5,6-position, A is the ethylene group and B is the methylene group, or A is the methylene group and B is the ethylene group, and each of X and Y is hydrogen or together are an additional bond, or a pharmaceutically acceptable acid addition salt thereof, the ratio of the first and second active ingredient being from 1:2 to 1:100, together with at least one conventional carrier or adjunct.

2. A pharmaceutical composition according to claim 1 which contains a compound of the formula I, in which Pip is the 4-hydroxy-4-(p-chlorophenyl)-piperidino, 4-hydroxy-4-[m-(trifluoromethyl)-phenyl]-piperidino or 4-hydroxy-4-(p-tolyl)-piperidino radical, or a pharmaceutically acceptable acid addition salt thereof.

3. A pharmaceutical composition according to claim 1 which contains a compound of the formula II, in which $R_1$ is hydrogen, an alkyl radical containing at most 4 carbon atoms, a 2-propynyl or cyclopropylmethyl radical, $R_2$ is hydrogen, $R_3$ is hydrogen, halogen having an atomic number up to 35, a methyl, methoxy or cyclohexyl group, $R_4$ is hydrogen, a methyl group, chlorine or bromine, A is an ethylene group and B is a methylene group, and X and Y together are an additional bond or each is a hydrogen atom, or a pharmaceutically acceptable acid addition salt thereof.

4. A pharmaceutical composition according to claim 1 which contains haloperidol or a pharmaceutically acceptable acid addition salt thereof, and 4-(5,6-dimethyl-2-benzofuranyl)piperidine or a pharmaceutically acceptable acid addition salt thereof.

5. A pharmaceutical composition according to claim 4 which contains both active ingredients in the reatio of 1:10 to 1:50.

6. A pharmaceutical composition according to claim 4 which contains 0.25 to 2.5 mg of the first active ingredient and 5 to 50 mg of the second active ingredient in a dosage unit or in a suitable amount of a formulation which is not in dosage unit form.

7. A pharmaceutical composition according to claim 4 which contains 0.5 to 1.0 mg of the first active ingredient and 10 to 25 mg of the second active ingredient in a dosage unit or in a suitable amount of a formulation which is not in dosage unit form.

8. A pharmaceutical composition according to claim 1, wherein the compound of the formula I is haloperidol or a pharmaceutically acceptable acid addition salt thereof.

9. A pharmaceutical composition according to claim 1, wherein the compound of the formula II is 4-(5,6-dimethyl-2-benzofuranyl)-piperidine or a pharmaceutically acceptable acid addition salt thereof.

10. A pharmaceutical composition according to claim 1 which contains a butyrophenone derivative I of the formula I defined in claim 16 or a pharmaceutically acceptable acid addition salt thereof, and a compound of the formula II as defined in claim 16, or a pharmaceutically acceptable acid addition salt thereof, in a ratio of from 1:4 to 1:50.

* * * * *